(12) United States Patent
Zientek

(10) Patent No.: US 6,179,873 B1
(45) Date of Patent: Jan. 30, 2001

(54) INTERVERTEBRAL IMPLANT, PROCESS FOR WIDENING AND INSTRUMENTS FOR IMPLANTING AN INTERVERTEBRAL IMPLANT

(76) Inventor: Bernhard Zientek, Starenweg 9, D-73630, Remshalden (DE)

( * ) Notice: Under 35 U.S.C. 154(b), the term of this patent shall be extended for 0 days.

(21) Appl. No.: 09/011,068

(22) PCT Filed: Jul. 26, 1996

(86) PCT No.: PCT/EP96/03306

§ 371 Date: Jun. 11, 1998

§ 102(e) Date: Jun. 11, 1998

(87) PCT Pub. No.: WO97/06753

PCT Pub. Date: Feb. 27, 1997

(30) Foreign Application Priority Data

Aug. 11, 1995 (DE) .............................................. 195 29 605

(51) Int. Cl.$^7$ ....................................................... A61F 2/44
(52) U.S. Cl. ........................................................ 623/17.11
(58) Field of Search .................................. 623/17, 17.16, 623/17.15, 17.14, 17.13, 17.12, 17.11

(56) References Cited

U.S. PATENT DOCUMENTS

| | | | |
|---|---|---|---|
| 5,554,191 | * | 9/1996 | Lahille et al. .......................... 623/17 |
| 5,766,252 | * | 6/1998 | Henry et al. ............................ 623/17 |
| 5,980,522 | * | 11/1999 | Koros et al. ............................ 606/61 |

* cited by examiner

*Primary Examiner*—David J. Isabella
*Assistant Examiner*—Alvin Stewart
(74) *Attorney, Agent, or Firm*—Jones, Tullar & Cooper, P.C.

(57) ABSTRACT

The present invention relates to an adjustable-height intravertebral implant, having an approximately cylindrical hollow body which has one or more openings (59, 59', 60, 60') and which is variably expandable by adjusting elements, and which has fixation elements for fixing it to vertebral bodies. The present invention also relates to a method for expanding this intravertebral implant as well as to instruments for performing the method.

15 Claims, 19 Drawing Sheets

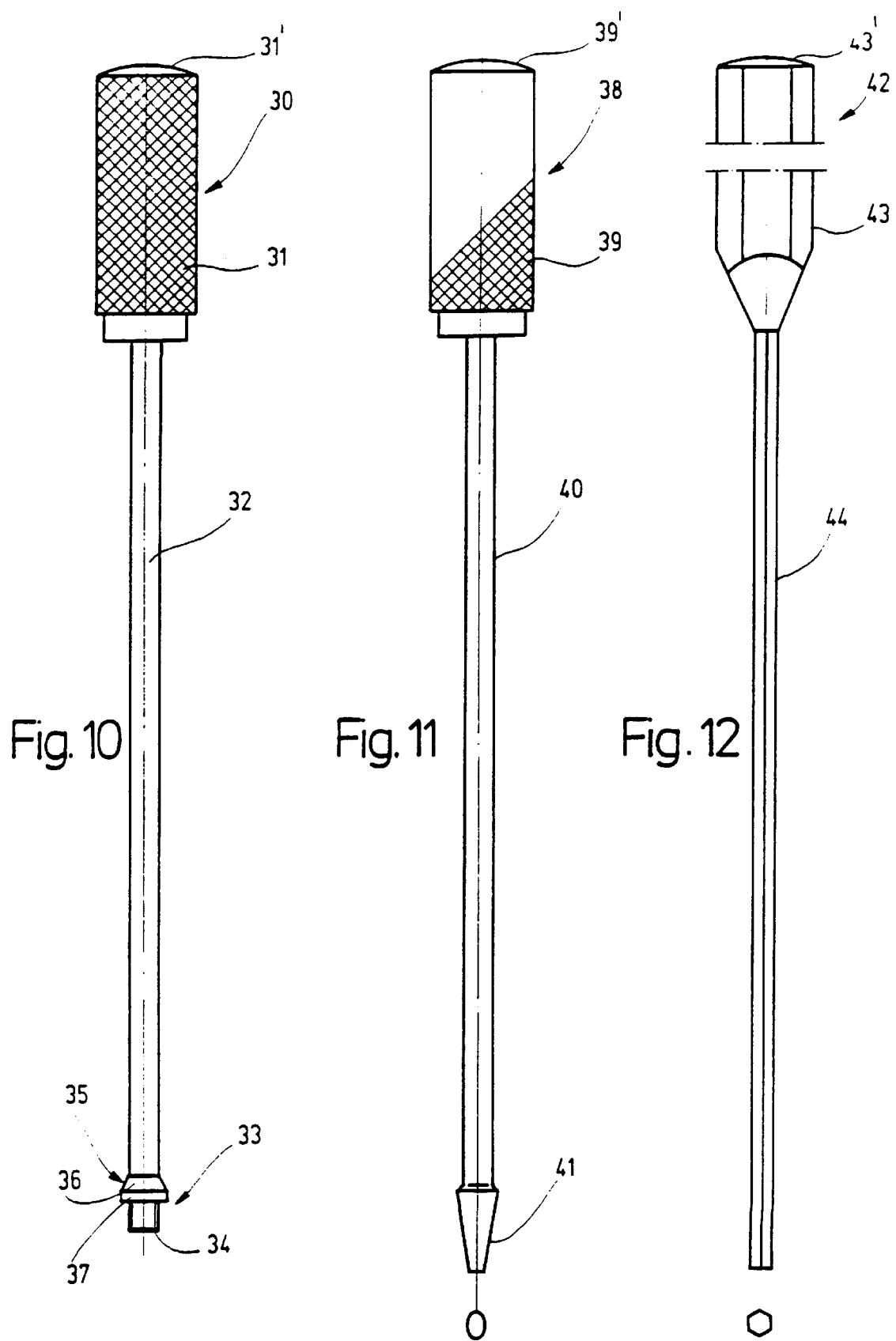

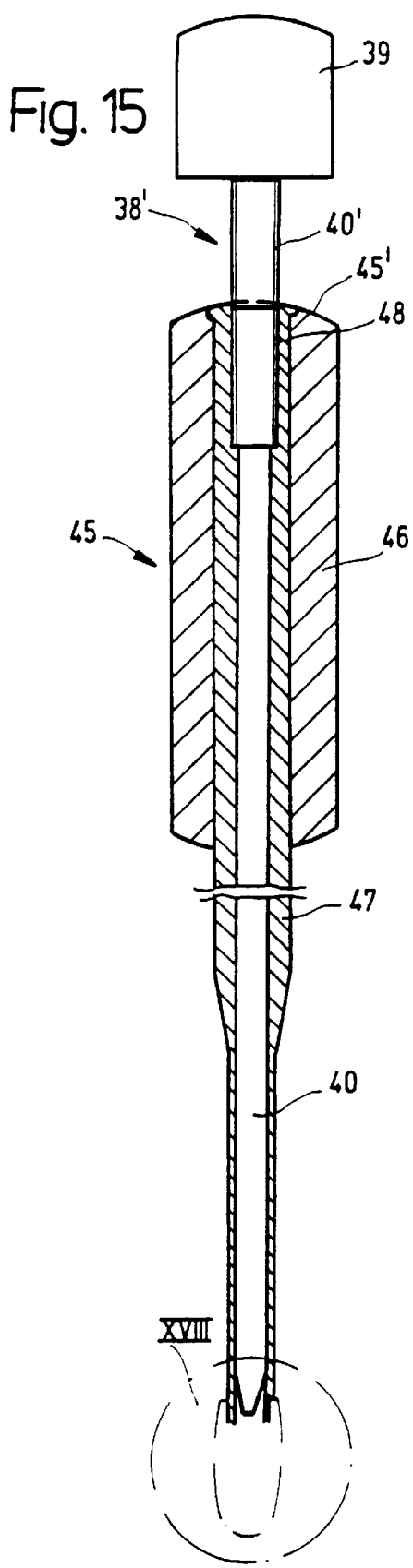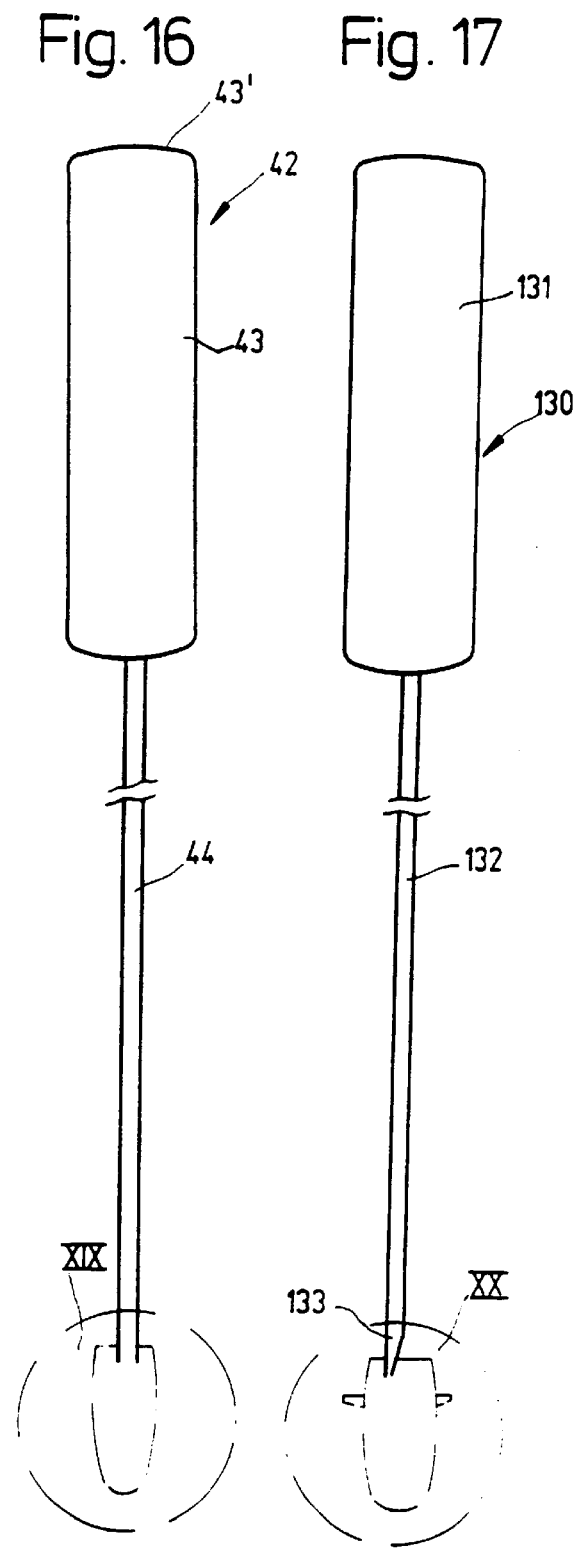

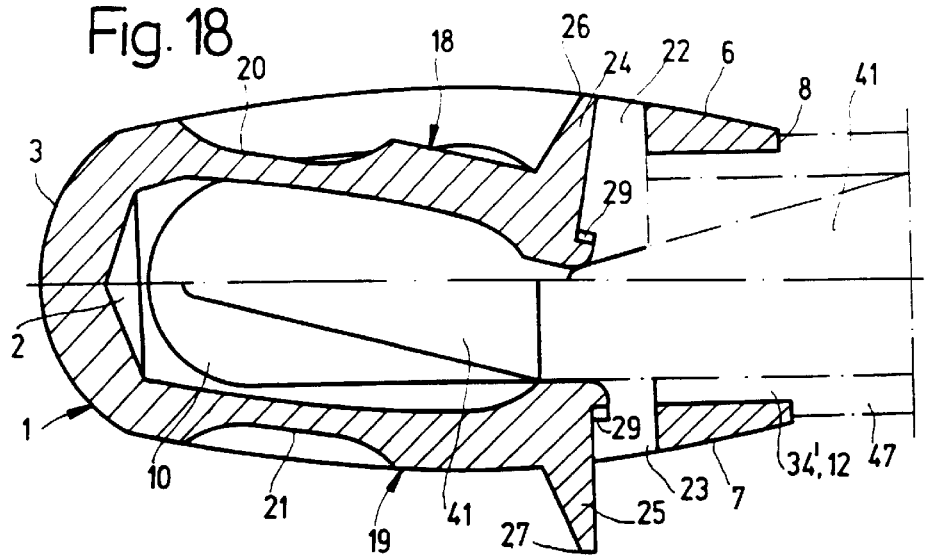
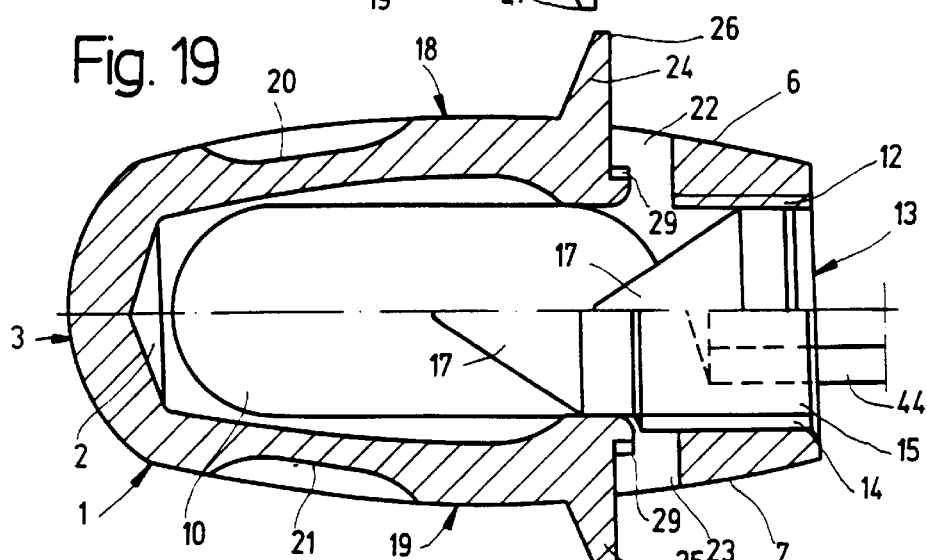
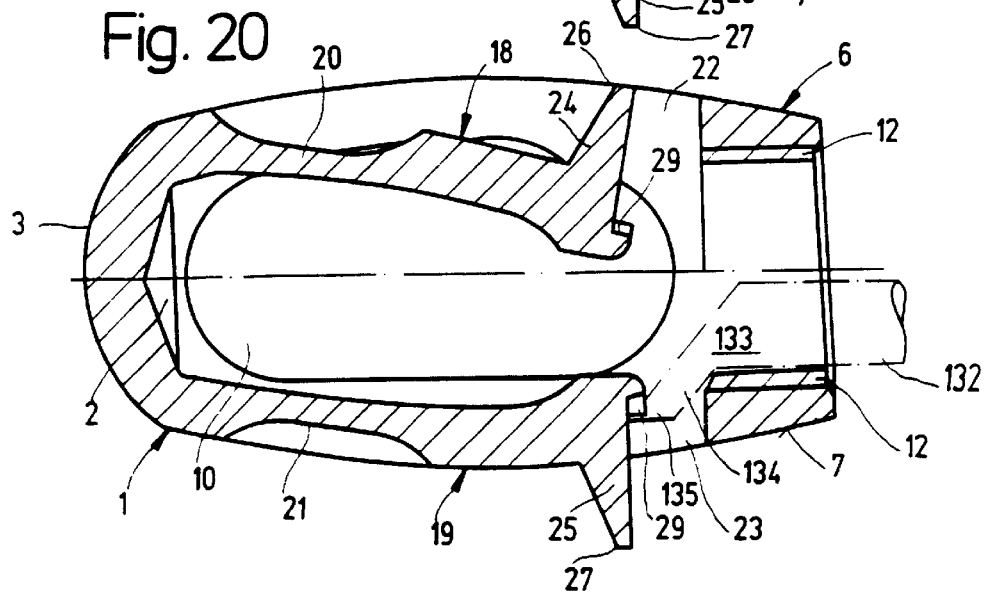

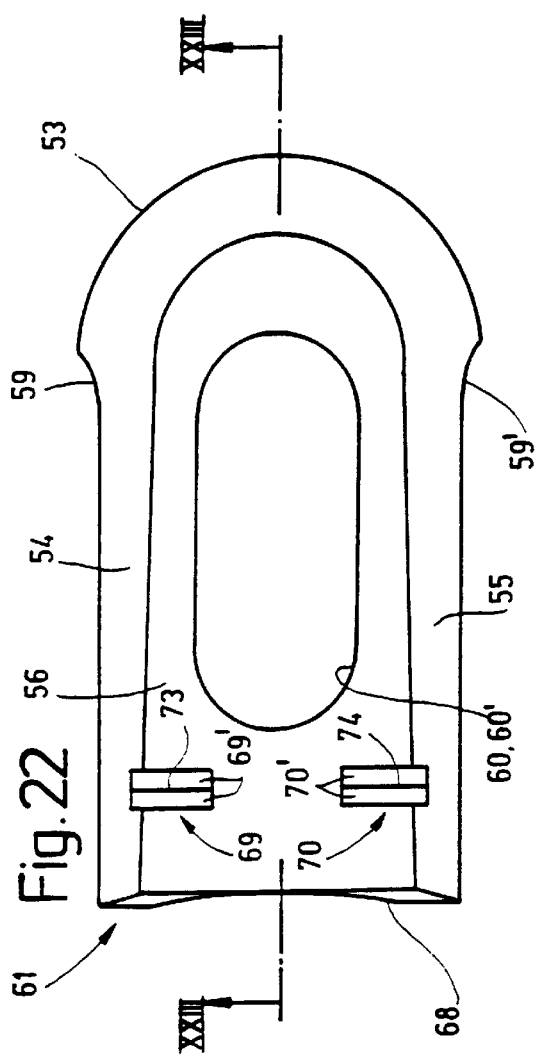
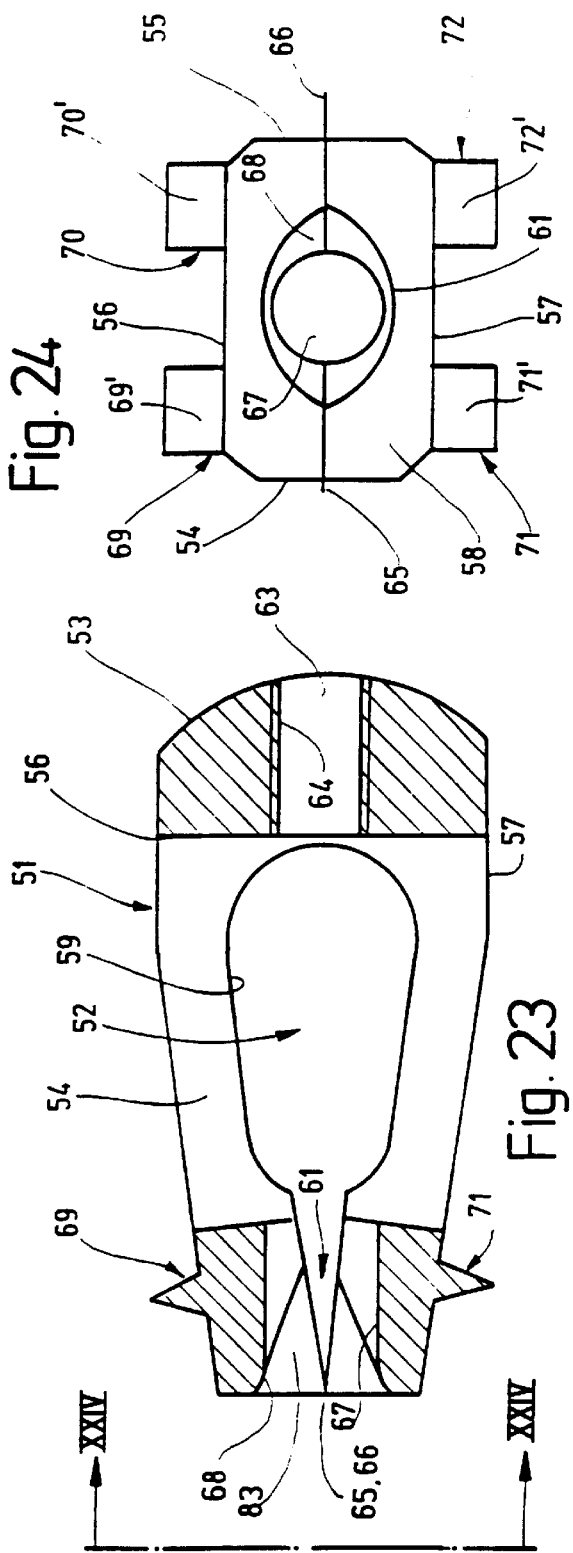

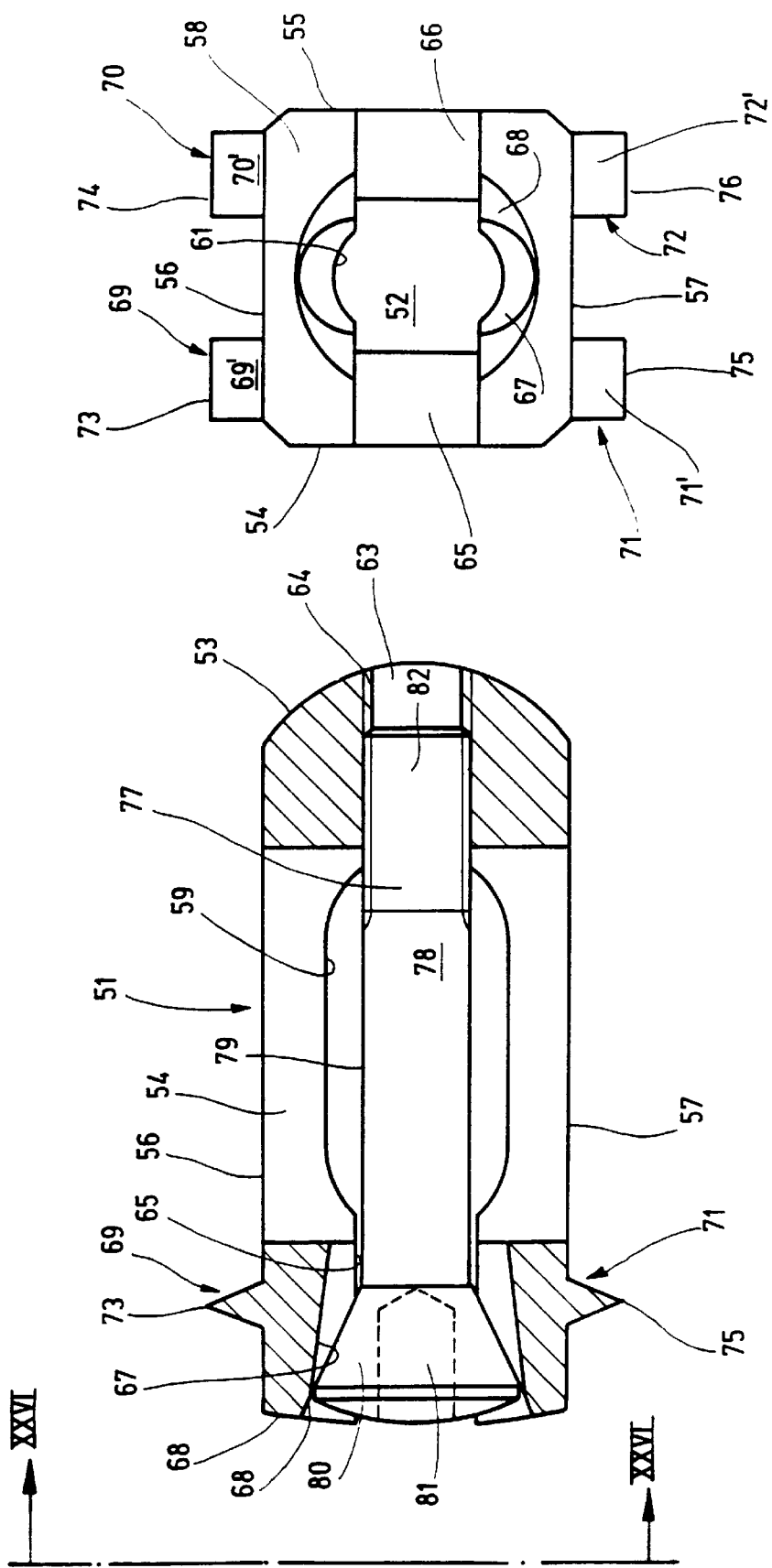

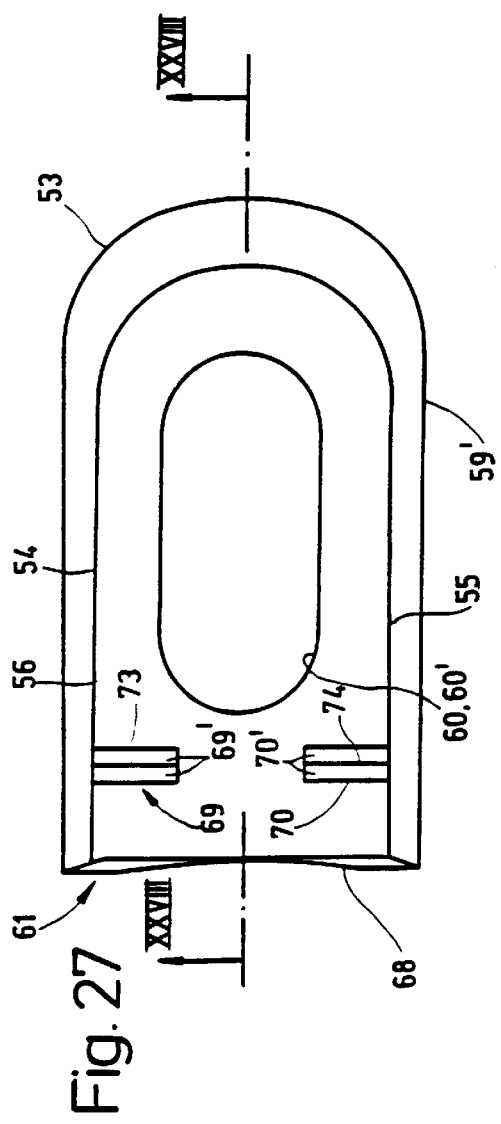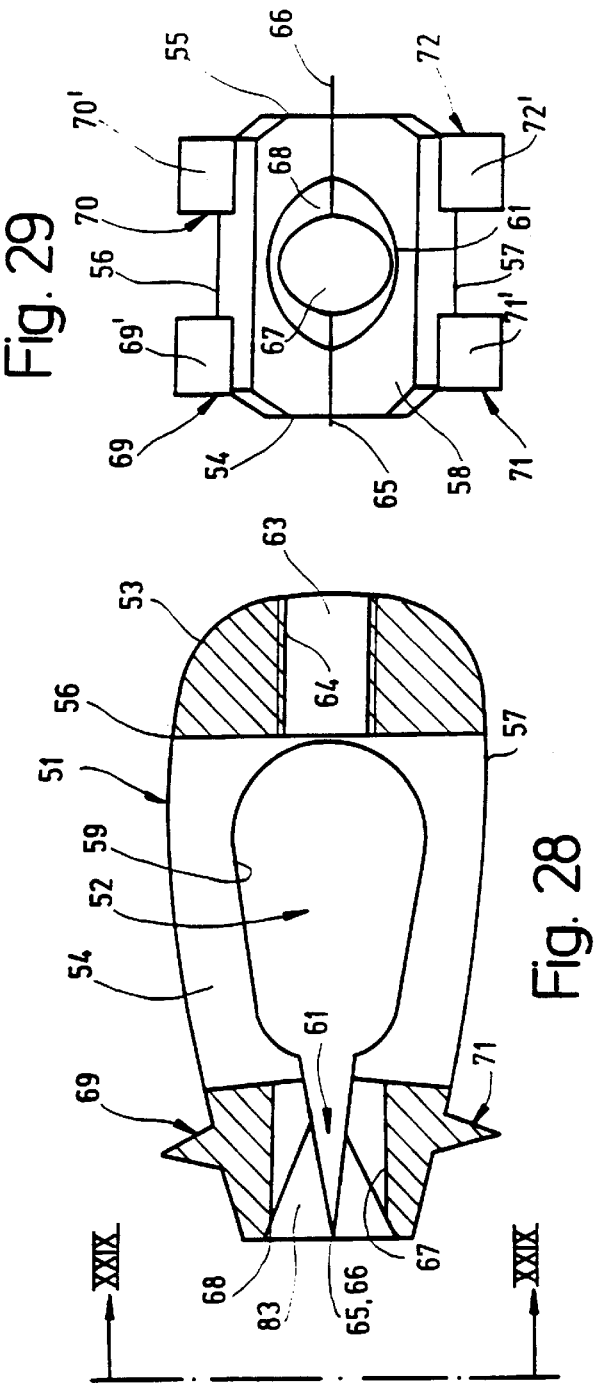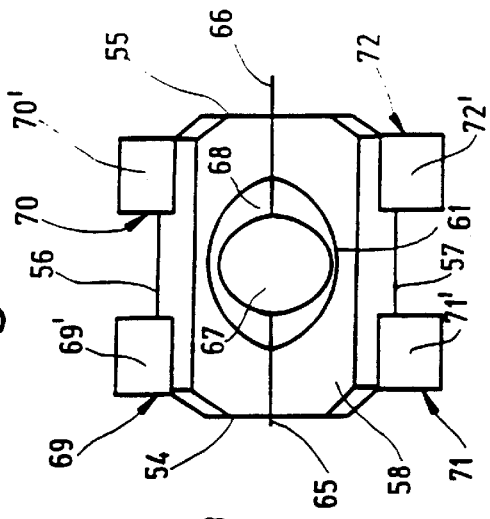

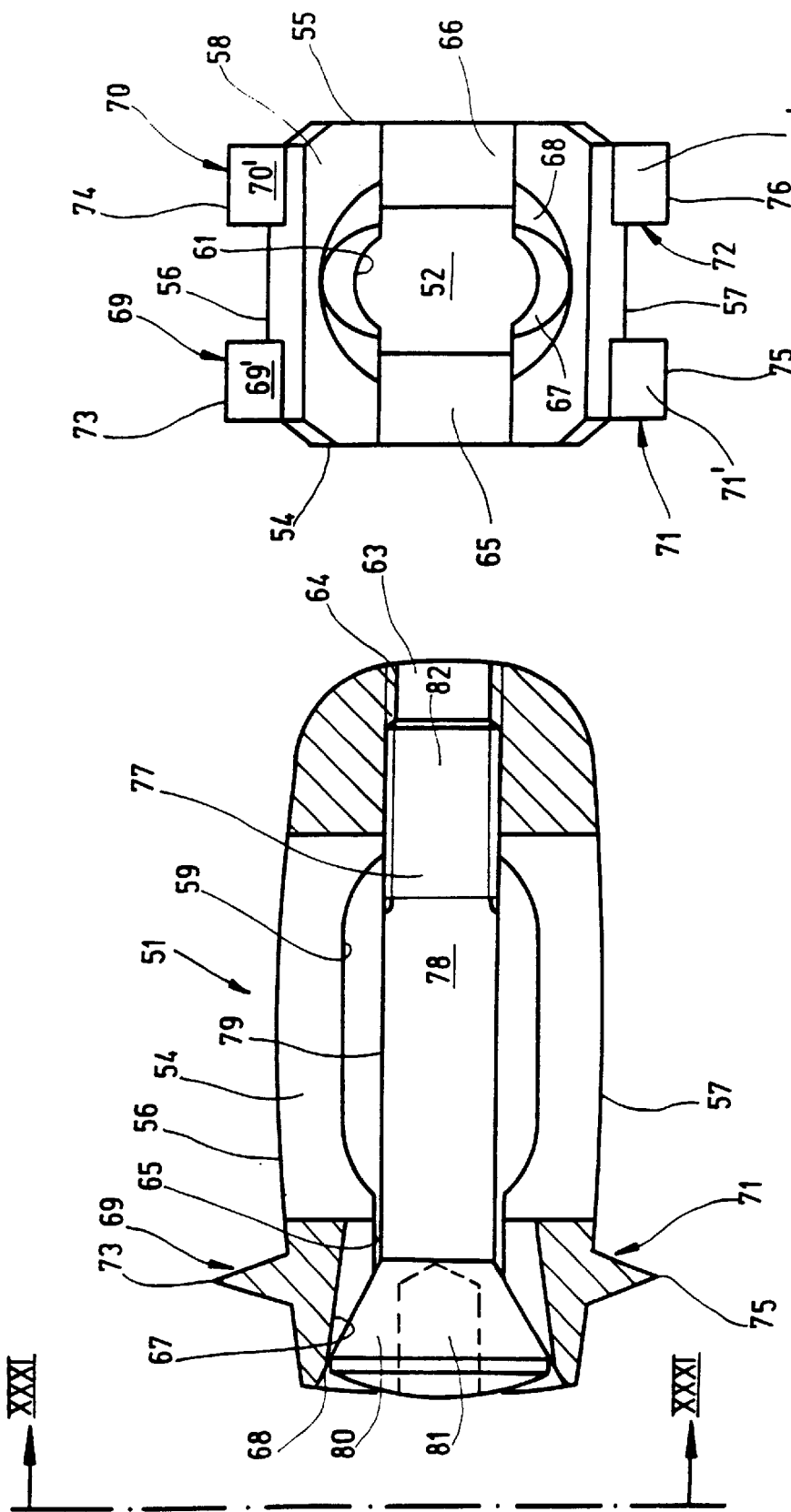

INTERVERTEBRAL IMPLANT, PROCESS FOR WIDENING AND INSTRUMENTS FOR IMPLANTING AN INTERVERTEBRAL IMPLANT

FIELD OF THE INVENTION

The present invention relates to an intravertebral implant, having an approximately cylindrical hollow body which has two ends, four side faces, and one or more openings, as well as to an instrument for implanting such an intravertebral implant and a method for expanding such an intravertebral implant.

BACKGROUND OF THE INVENTION

Between the individual vertebral bodies of the spinal column, the intravertebral disks are located, better known as simply "disks". The disks comprise an outer ring of connective tissue and cartilage and an inner gelatinous core, and they serve as elastic buffers between the vertebral bodies. The inner gelatinous core can shift, however, or prolapse through cracks in the outer ring. This disorder is known as prolapse or herniation of the disks. In severe cases, nucleotomy or diskotomy is necessary; that is, the disk has to be removed. After that the vertebral bodies have to be fused; that is, the spacing between them must be maintained by suitable provisions; otherwise, they would slip into the gap that was previously filled by the disk. This would cause compressions in this region of the spinal column; the spinal cord would be compressed and stretched in the vicinity of the affected vertebral bodies. The consequence would be pain and neurological defects.

Fusion of the vertebral bodies can be done for example by means of intravertebral implants.

One known intravertebral implant is known by the term PLIF (for posterolateral interbody fusion), in which cagelike hollow bodies (intersomatic cages) are inserted between the vertebral bodies. To that end, in the region previously occupied by the disk, a space into which the hollow body is driven is created by roughening the adjacent vertebral bodies or removing their periosteum and the cortical substance. A disadvantage of this is that in this method additional stabilization is always necessary, for instance internal fixation by means of four pedicle screws connected to two rods. Even then, the hollow bodies can slip because they grow into the implant only gradually. This is due to the fact that the cortical substance, which is jointly responsible for bone grown, is involved. Especially, the implants can be forced away toward the rear, until they have grown firmly into place.

Another possibility known from the prior art is to implant screwable hollow cylinders for lumbar interbody fusion. These implants are hollow cylinders with a male thread. This means that a thread has to be cut into the vertebral body adjacent to the disk space. The hollow cylinders are then screwed into that thread. In this method, it is true that the implants can no longer slip, but the method is extremely complex, which also entails the risk of complications.

The necessity of injuring the periosteum and the cortical substance of the vertebral bodies is also felt to be a disadvantage, because these structures are hard and solid and normally have a stabilizing effect. The bone growth and thus the fusion are slowed down by the injury to the cortical substance.

One disadvantage common to both these known intravertebral implants is their fixed dimensions. However, the spacing to be maintained between the affected vertebral bodies is different for each patient. Hence numerous versions with different dimensions are needed. Nevertheless, it cannot be avoided that the intravertebral implants are not seated optimally, for instance being seated too firmly or too loosely.

The object of the invention is therefore to furnish an adjustable intravertebral implant of the above type, with which the above-described disadvantages are avoided and with which in the simplest possible way, fast and durable fusion of vertebral bodies is made possible.

This object is attained in that the hollow body can be expanded on at least two opposed sides and locked in the expanded position by an adjusting element that can be introduced into the hollow body, and the expansion is done on the end at which the adjusting element can be introduced.

The object of the invention is also to furnish a fast, simple method for expanding an intravertebral implant.

The method according to the invention contemplates the following method steps:

(a) prewidening the hollow body;

(b) expanding the hollow body.

The object of the invention is also to furnish instruments for implanting an intravertebral implant.

Instruments according to the invention are defined by the characteristics recited in claims 17, 22, 23 and 24.

The intravertebral implant of the invention has fixation elements which secure it on the vertebral bodies so that it will not change position. These elements anchor the intravertebral implant to the vertebral bodies. The expansion can be done to a variable extent, so that variable dimensions are available. That is, the diameter of the intravertebral implant and hence the spacing of the vertebral bodies from one another are adjustable. Thus the correct size and in particular the correct diameter for every patient is always available. Moreover, the intravertebral implant is always precisely correctly seated, namely not too firmly and not too loosely. The play is approximately 1 to 2 mm. Substantially fewer intravertebral implants of different dimensions are needed for the varying vertebral body spacings of the patients. The widening elements are also used to retract the fixation elements into the "insertion position", so that the hollow body can be driven in without hindrance between the vertebral bodies. Only after that is the expansion done, which thus brings about the fixation of the fixation elements on the vertebral bodies.

The expansion of the intravertebral implant can be done in various ways. One possibility is to provide spreader tongues, which are cutout from the hollow body and can be bent outward and which have fixation elements on their outer surface. Another possibility is for the hollow body itself to have a slot of a certain width, which thus divides it into two halves that can be pressed together or expanded. In that case, the play is not defined by the diameter of the hollow body itself.

It is especially advantageous for the intravertebral implant of the present invention to be designed with a somewhat crowned or bellied form. Thus it is especially well adapted to the contours of the space, formed by the surfaces of the vertebral bodies, that was previously filled by the disk.

The expansion of the intravertebral implant according to the present invention is preferably done in two steps. Since the expandable regions are first contracted, it is prewidened in a first step, until the fixation elements touch the vertebral bodies. In a second step, it is then widened to the final extent and thus fixed on the vertebral body. The fixation elements have advantageously have a relief the inside of which can be engaged by a retrieval instrument, so that they can optionally be pulled back in again after the expansion.

The instruments necessary for the implantation include an implant holder, with which the intravertebral implant of the present invention can be guided easily and securely until its final fixation. This implant holder is preferably hollow and can receive other instruments within it as well, such as a distractor for the prewidening or an insertion instrument for introducing the adjusting element. Hence it is assured that the location and seating of the intravertebral implant can be monitored at all times during the insertion process.

The subject of the present invention is also an instrument for measuring the spacing between two vertebral bodies. It is thus possible to find out what size of implant is needed or how much the implant has to be expanded.

BRIEF DESCRIPTION OF THE DRAWINGS

Exemplary embodiments of the present invention will be described in further detail below in conjunction with the accompanying drawings. Shown are:

FIGS. 10–12, which show three instruments for implanting the exemplary embodiments shown in FIGS. 1 and 5;

FIG. 15, which is an illustration of the distractor shown in FIG. 14, in the implant holder shown in FIG. 13;

FIGS. 16 and 17, which show two further instruments;

FIGS. 18 and 19, which show enlarged details of region XVIII of FIG. 15 and XV of FIG. 16, which in the upper half of the drawings show the implant with the instrument before actuation and the lower half shows the instrument or element after actuation;

FIG. 20, which is an enlarged detail of region XX of FIG. 17, in which the upper half shows the implant after actuation and the lower half shows the implant with the instrument before actuation;

FIG. 22, which is a plan view of a third exemplary embodiment of an intravertebral implant according to the present invention;

FIG. 23, which is a section taken along the line XXIII—XXIII of FIG. 22 in the insertion state;

FIG. 24, which is a view in the direction of the arrows XIV—XIV of FIG. 23;

FIG. 25, which is a view as in FIG. 23 but in the spread-open state;

FIG. 26, which is a view in the direction of the arrows XVI—XVI of FIG. 25 in the spread-open state, without the screw 77;

FIGS. 27–31, which are views of a fourth exemplary embodiment, functionally identical to the third exemplary embodiment of FIGS. 22–26;

DESCRIPTION OF THE PREFERRED EMBODIMENTS

Figure 1:
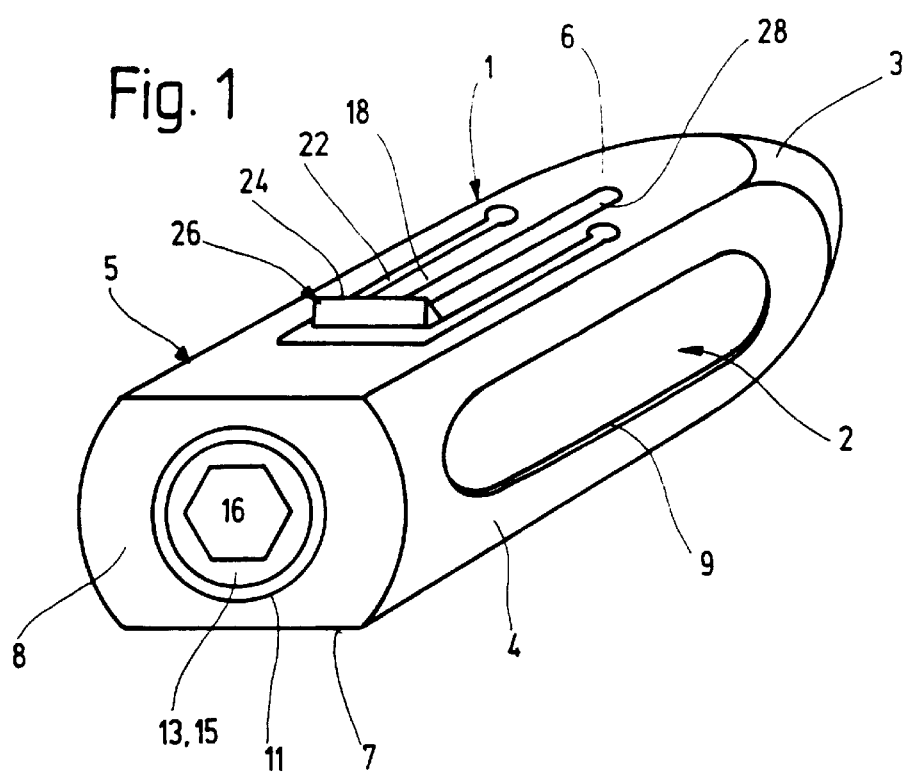
FIG. 1, which is a perspective view of a first exemplary embodiment.
Figure 2:
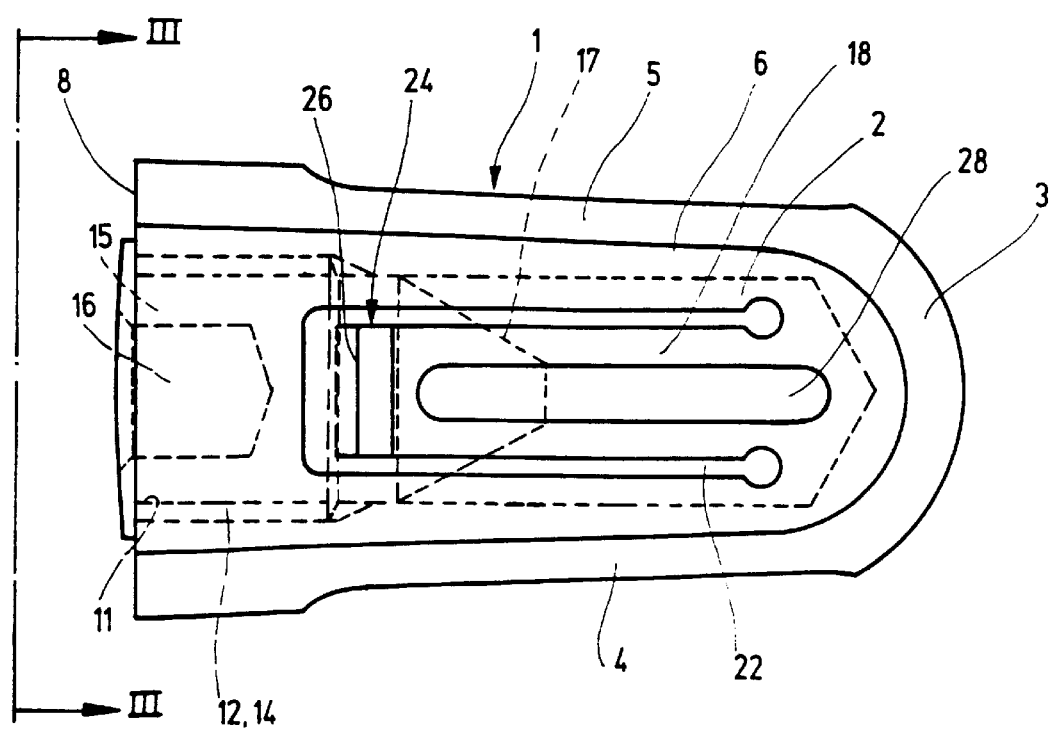
FIG. 2, which is a side of the exemplary embodiment shown in FIG. 1.
Figure 3:
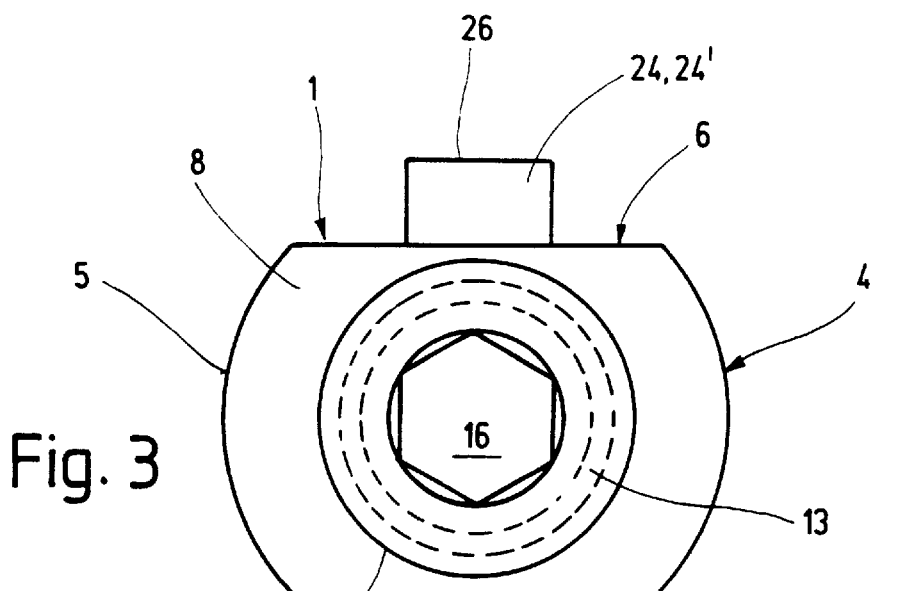
FIG. 3, which is a view in the direction III—III of FIG. 2.

The exemplary embodiments described below are parts made of titanium or optionally also of carbon. Titanium is tissue-compatible and has a high modulus of elasticity, so that it is an extreme highly suitable material for the intravertebral implants of the present invention.

The intravertebral implants shown in FIGS. 1–4 and 5–8, respectively, are functionally identical and are also structurally identical in substantial parts. In the drawings, identical parts are identified by the same reference numerals.

The intravertebral implants are approximately 25 mm long, 11–14 mm wide, and 9 to 13 mm high. They have a hollow body 1, which encloses a hollow chamber 2. The hollow body 1 is approximately cylindrical and is provided with a dome 3, four side faces 4, 5, 6, 7, and a back face 8. Oval openings 9, 10 are formed in the side faces 4, 5, extending over approximately half to two-thirds of the side faces 4, 5. Located on the back face 8 is an approximately centrally disposed bore 11 with a female thread 12, into which a screw 13 with a male thread 14 is screwed. The head 15 of the screw 13 has a hexagonal socket 16. The screw forms the aforementioned expander element.

Approximately rectangular spreader tongues 18, 19, each approximately 4 mm wide and each defined by a U-shaped slot 22, 23, are located in the two side faces 6, 7. A cramp 24, 25 is integrally formed onto the free end of each spreader tongue 18, 19. The cramps 24, 25 are triangular in cross section, in such a way that the free edges 26, 27 protrude outward. The free edges 26, 27 are embodied as sharp, for instance being ground down. The cramps form the aforementioned fixation elements.

Figure 5:
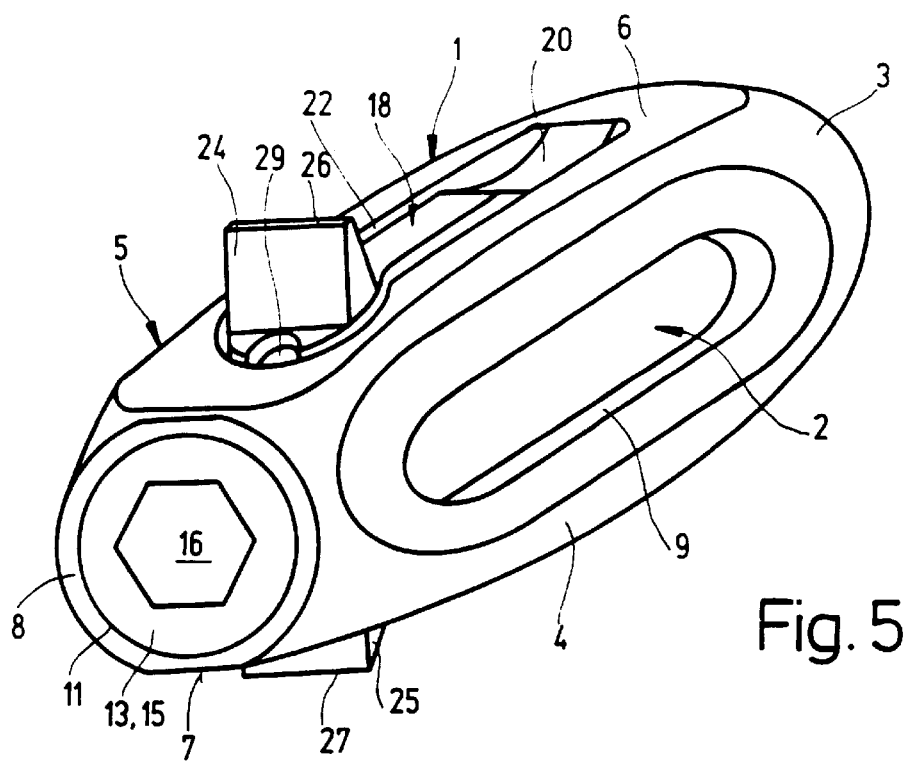
FIGS. 5–8 which show a second exemplary embodiment, functionally identical to the first, seen in FIGS. 1–4.
Figure 6:
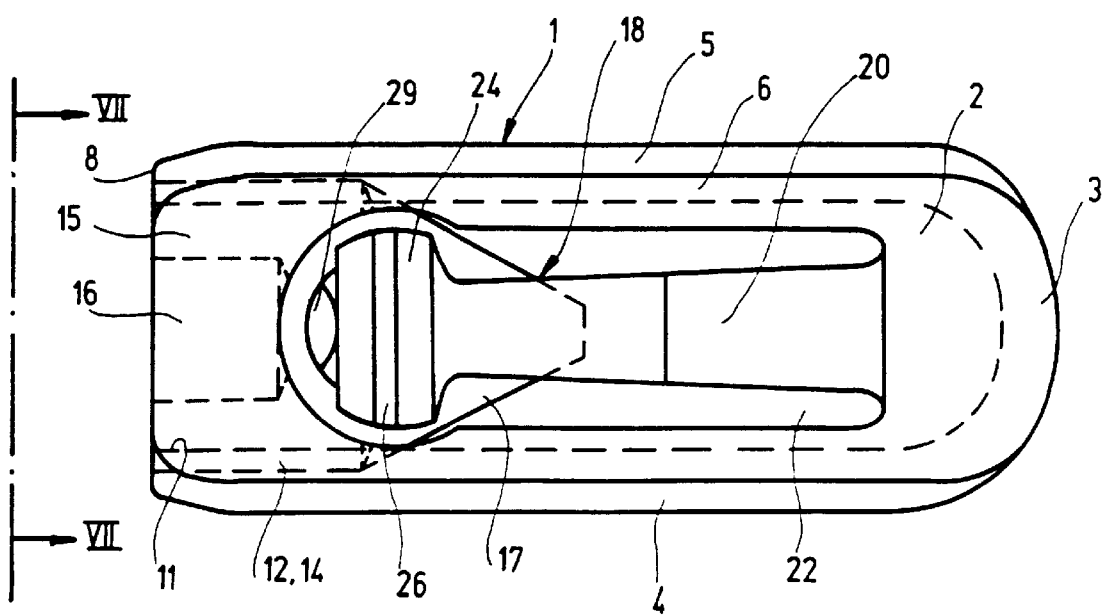
Figure 7:
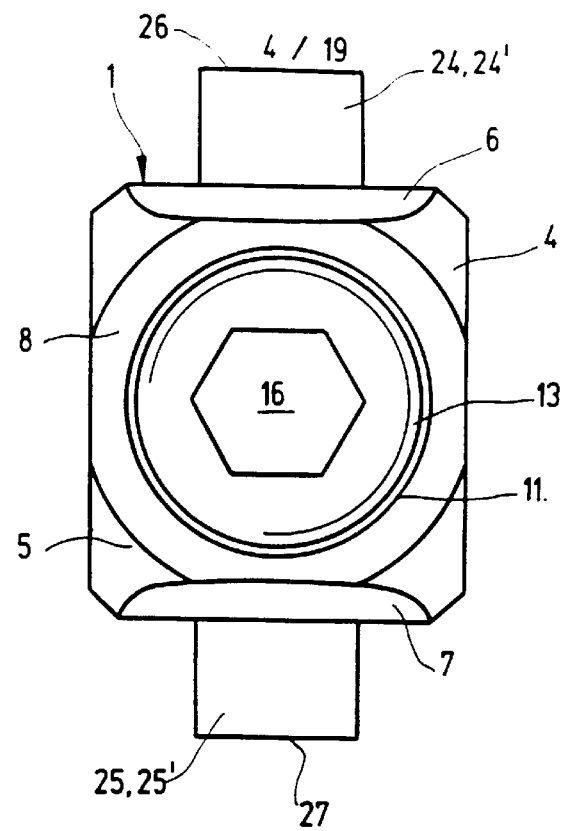
Figure 9:
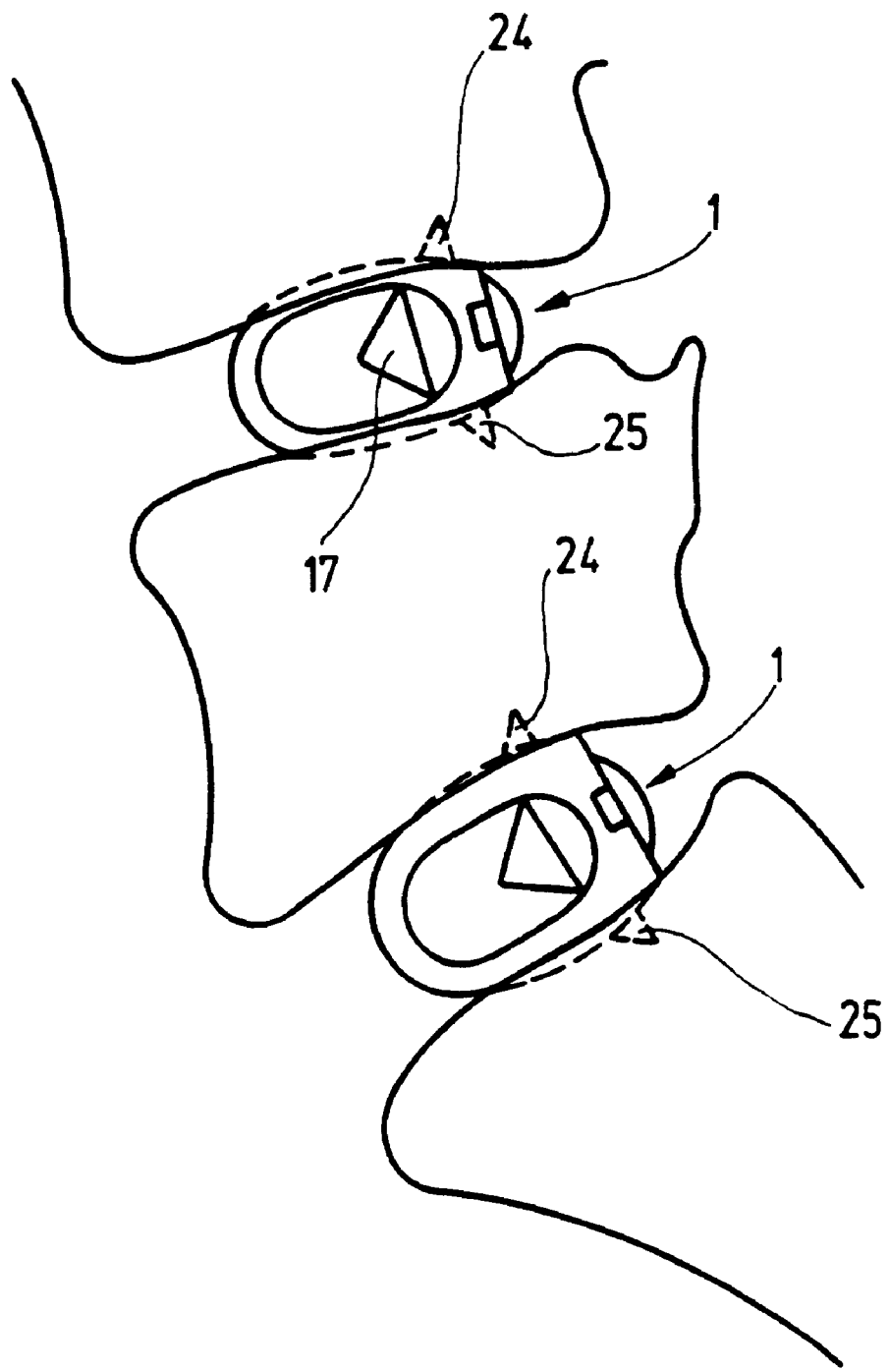
FIG. 9, which is a schematic illustration of two implanted exemplary embodiments of FIG. 5.

The exemplary embodiments shown in FIGS. 1 and 5, while being identical in function, have structural differences. The exemplary embodiment in FIG. 1 has two flat side faces 6, 7 and two curved side faces 4, 5, while the second exemplary embodiment in FIG. 5 has an entirely curved, "crowned" or "bellied" contour and is approximately square in cross section. The advantage of this contour is schematically shown in FIG. 9. The faces of the vertebral bodies that enclose the hollow chamber in which the disk was previously located have a slightly concave contour. The more convex contour of the implant corresponds with this in such a way that it contacts the vertebrae over a large surface area and in a sense "mates with" the contours of the hollow chamber.

The spreader tongues 18, 19 of the first exemplary embodiment (FIG. 1) also have oblong slots 28, so that the bone tissue can more rapidly penetrate the hollow chamber 2. In the second exemplary embodiment (FIG. 5) the oblong slots 28 have been dispensed with. Instead, the spreader tongues 18, 19 are narrower and are provided with curved spring elements 20, 21, which lend them greater elasticity. The spreader tongues 18, 19 of the second exemplary embodiment also have a relief 29, into which in the spread-open state a retrieval instrument can be inserted, so that when the retrieval instrument is braced against the shoulder of the thread 12 for the screw 13, the spreader tongues 18, 19 can be retracted into the hollow chamber 2 again (for further detail see below). The relief 29 is embodied as round, so that the retrieval instrument cannot slip away to the left or right.

Figure 4:
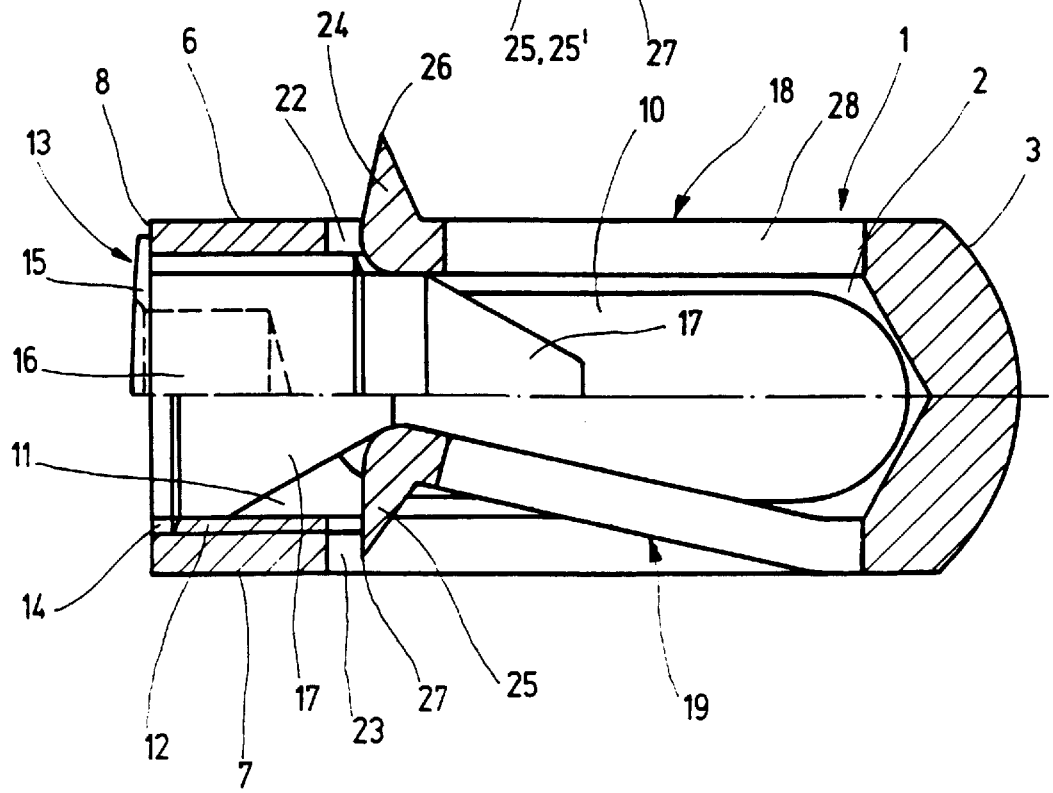
FIG. 4, which is a longitudinal section through the exemplary embodiment shown in FIG. 1, in which the upper half of the drawing shows the spread-open state, while the lower half shows the insertion state which is not yet spread open.
Figure 8:
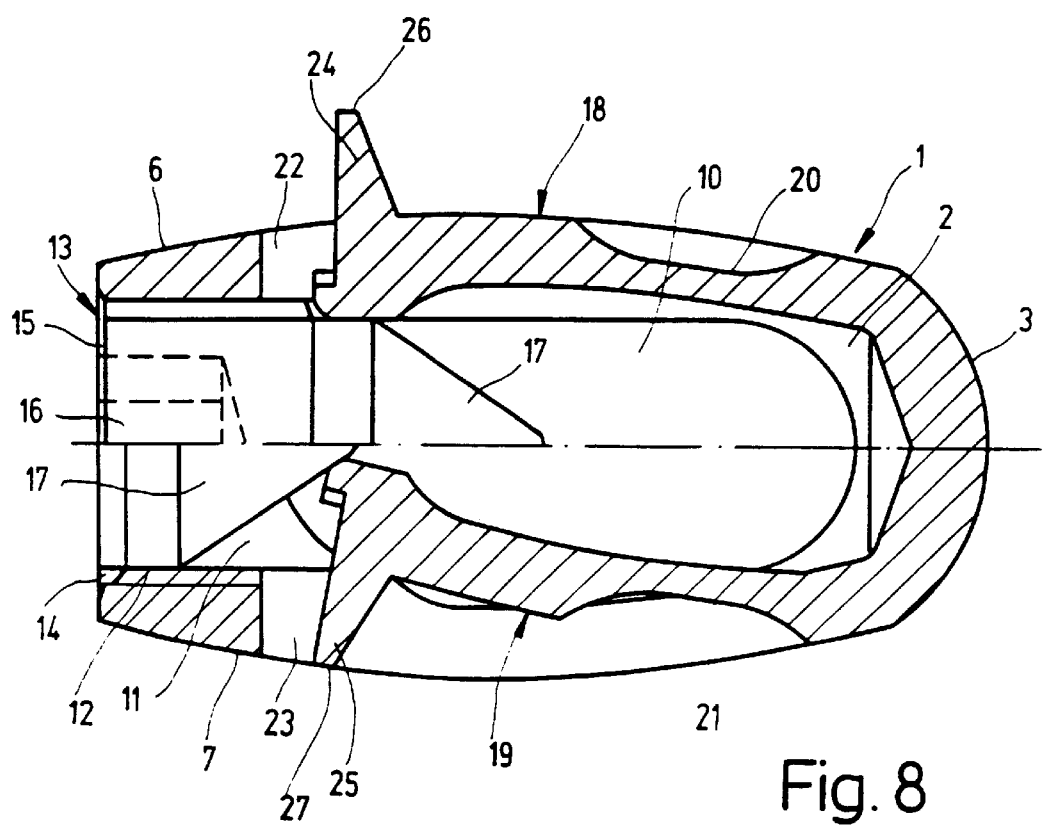

In FIGS. 4 and 8, respectively, the mode of operation of these exemplary embodiments is shown. FIGS. 10–12 show schematic exemplary embodiments of the instruments required for them. These are in implant holder 30 (FIG. 10), a distractor (FIG. 11), and a hexagonal socket wrench 42 (FIG. 12). A common feature of all the instruments 30, 38, 42 is that they have a grip 31, 39, 43; a long shaft 32, 40, 44; and an end 33, 41, 45, respectively. In the state (FIG. 4 and 8, bottom) in which the hollow bodies 1 are inserted between vertebral bodies (insertion state), the spreader tongues 18, 19 are forced inward into the hollow chamber 2, so that the free edges 26, 27 of the cramps 24, 25 do not protrude past the side faces 6, 7 of the hollow body 1. The leading end 33 of the implant holder 30, which is provided with a male thread 34, is screwed into the female thread 12 of the bore 11. The intravertebral implant thus fixed on the implant holder 30 and formed by the hollow body 1 is driven in between two vertebral bodies. Once the intravertebral implant is located at the desired point, the end 33 of the implant holder 30 is unscrewed out of the bore 11 of the hollow body 1 forming the intravertebral implant. Now, with the aid of the distractor 38 (FIG. 11), whose end 41 as indicated is approximately elliptical in cross section, the spreader tongues 18, 19 are forced gradually outward, and the sharp edges 26, 27 of the cramps 24, 25 are gradually forced into the cortical substance of the vertebral bodies. Next, with the aid of the screwdriving instrument 42, the hexagonal socket screw 13 is screwed into the female thread 12 of the bore 11 (FIGS. 4 and 8, bottom). The screw 13 is long enough that viewed in cross section, it protrudes with its leading, conically tapering end 17 past the height of the cramps 24, 25 into the hollow chamber 2 of the hollow body 1 (FIGS. 4 and 8, top) and thus on being screwed in forces the spreader tongues 18, 19, and with them the cramps 24, 25, apart. The thickness of the end 17 is approximately equivalent to the diameter of the hollow chamber 2, so that when the screw is screwed in the spreader tongues 18, 19 are locked and the location of the hollow body 1 between the vertebral bodies is fixed.

An alternative procedure is for the spreader tongues 18, 19 to be forced outward only gently with the aid of the distractor, until the edges 26, 27 of the cramps 24, 25 rest on the respective vertebral bodies and are pressed only slightly into periosteum of the vertebral bodies. Not until the screw 13 is screwed in are the sharp edges 26, 27 of the cramps 24 and 25 pressed to their final extent into the cortical substance of the vertebral bodies.

Figure 13:
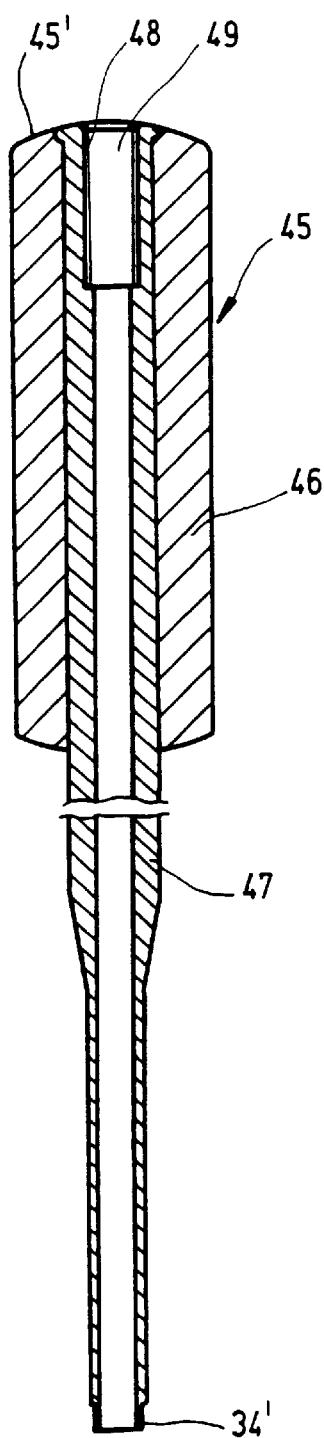
FIG. 13, which is an exemplary embodiment of an implant holder according to the present invention for the implants shown in FIGS. 1 and 5.

FIG. 13 shows a further exemplary embodiment of an implant holder 45, with a hollow grip 46 that is penetrated all the way through by a likewise hollow shaft 47. The free end of the hollow shaft 47 has a male thread 34. The end of the hollow shaft 47 toward the grip has a female thread 48. The impact face 46' of the grip 46 has a through opening 49, which gives access to the hollow shaft.

Figure 14:
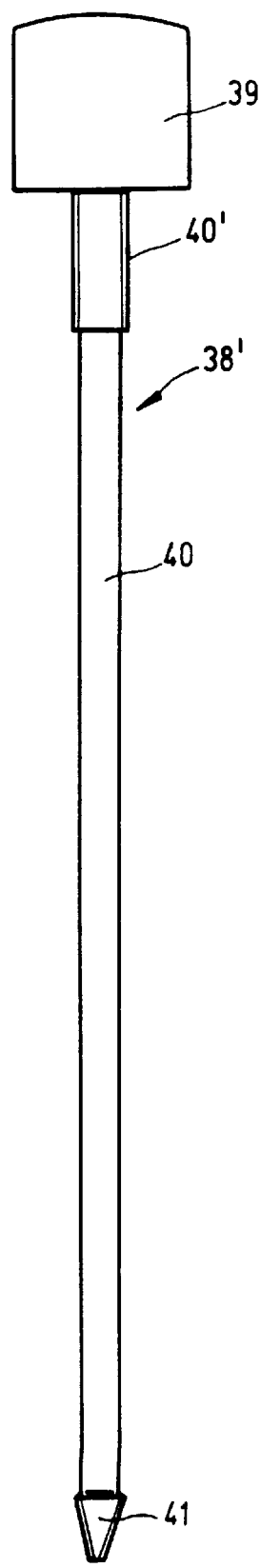
FIG. 14, which is an exemplary embodiment of a distractor.

The function of this implant holder 45 is the same as has already been described for the implant holder 30 shown in FIG. 10. The front end of the implant holder 45 is screwed with its male thread 34 into the female thread 12 of the hollow body 1. In this way, the implant is held while it is being inserted by the surgeon. Once the implant is seated at the correct point, the leading end of the hollow shaft 45, with the male thread 34, stays screwed into the female thread 12 of the bore 11 of the hollow body 1. The distractor 38' shown in FIG. 14, whose shaft 40 is provided, on its end toward the grip 39, with a male thread 40', is inserted into the hollow shaft 47 of the implant holder 45. This situation is shown in FIG. 15. The thread 40' on the end toward the grip of the distractor 38' engages the thread 48 on the end toward the grip of the hollow shaft 47. Turning the distractor 38' screws it to the implant holder 45. This effects a controlled displacement of the distractor 38', so that its tip 41 gradually penetrates the hollow chamber 2 of the hollow body 1 and expands the spreader tongues 18, 19. In this way, the intravertebral implant can be widened in a controlled fashion, and via the implant holder 45 full control over the position and the seat of the implant is simultaneously maintained.

The initial and final stages of this process are also shown again, on a larger scale, in FIG. 18; the upper part of the figure shows the situation corresponding to FIG. 15, namely after the insertion and before the distractor 38' is screwed in. The lower part of FIG. 18 shows the situation once the distractor 38' has been screwed all the way into the implant holder 45. The intravertebral implant is now fully widened. It is understood that the expansion can be terminated in any intermediate stage and the distractor 38' then unscrewed out of the implant holder 45. The desired final point can be defined for instance by suitably limiting the depth to which the two threads 47, 40' can be screwed together.

The implant is now "seated". The distractor 38' is then unscrewed out again and pulled out of the implant holder 45. Next, the implant holder is unscrewed out of the hollow body 1. The screw 13 is set against a hexagonal socket wrench 42 (FIG. 16), which is equivalent to the instrument shown in FIG. 12 and is therefore identified by the same reference numeral. The screw 13 is screwed into the hollow body 1 by slowly turning the screwdriving instrument 42. This situation is shown in FIG. 19, bottom part. Once the screw 13 has been screwed all the way in, the screwdriver 42' is set aside. This completes the spreading of the tongues 18, 19 that has been done with the aid of the distractor 38', and the intravertebral implant is now fixed. This situation is shown in FIG. 19, top. Naturally it is also possible to expand the implant only partially in the first step and to complete the expansion with the aid of the screw, simply pulled out of the implant holder 30'.

In FIG. 17, a retrieval instrument 130 is shown which is employed whenever the intravertebral implant of FIG. 5 must be removed, for whatever reason. The retrieval instrument 130 has a grip 131, a shaft 132, and a tip 133. While the drawing in FIG. 17 is purely schematic, the view in FIG. 20 is a detailed illustration of the construction of the tip 133 of the retrieval instrument 130. In this exemplary embodiment, the tip 133 is adapted in such a way that it is kinked twice, on the order of an offset bend and has both a portion 134 and a portion 135 that is parallel to the shaft 132. This kink is dimensioned such that after the screw 13 has been unscrewed from the hollow body 1 and the retrieval instrument 130 has been inserted, the portion 135 of the tip 133 engages the relief 29 of the spreader tongues 18, 19. By bracing the retrieval instrument 130 against the shoulder of the thread 12 for the screw 13, the spreader tongue 18, 19 can be bent back into the hollow chamber 2 again. This is shown in FIG. 20, top part.

Figure 21:
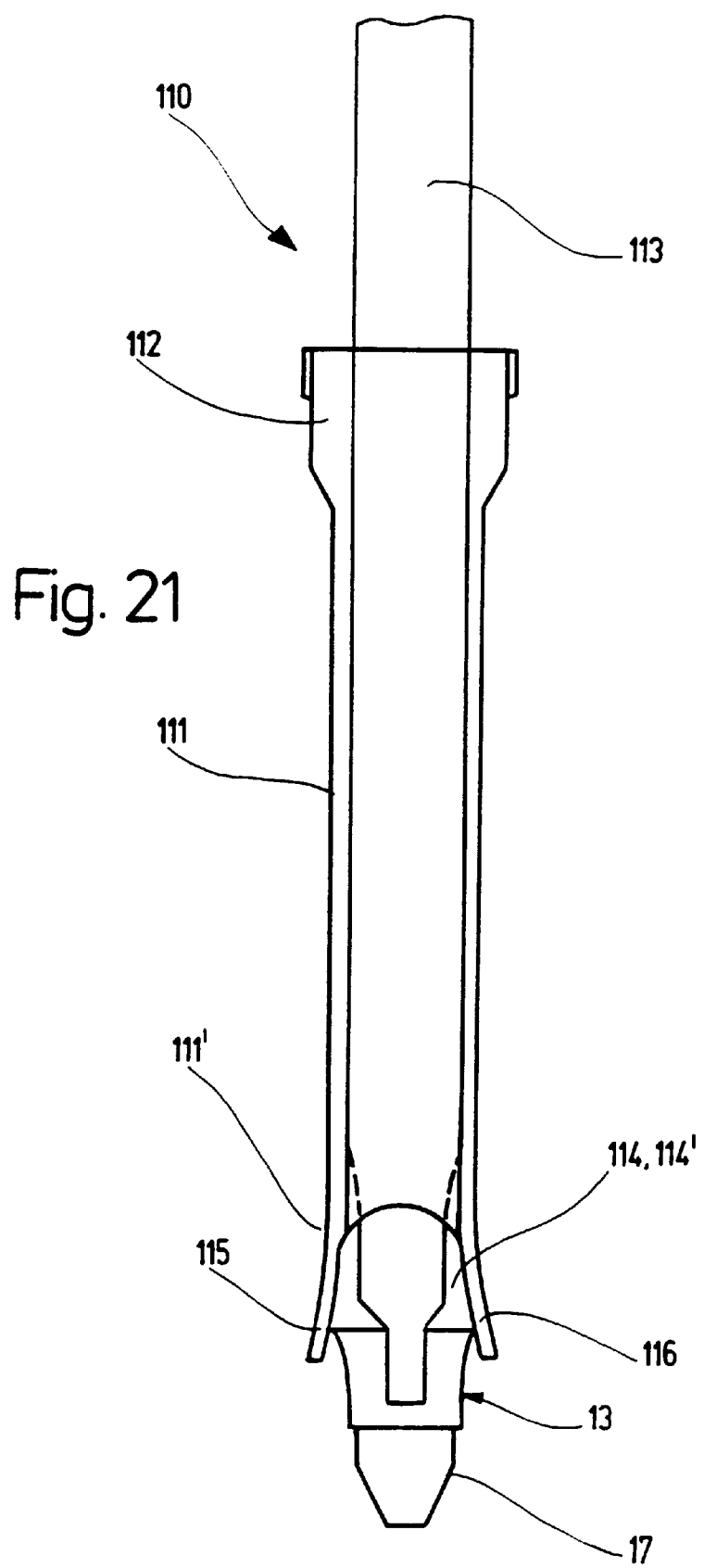
FIG. 21, which is a further instrument for implantation.

FIG. 21 shows a further exemplary embodiment of a hexagonal socket wrench 110, comprising a bushing 111 with a grip region 112 and the shaft 113 of the actual screwdriving instrument itself, which is guided in the bushing 111.

Located in the leading end 111' of the bushing 111 are two U-shaped notches 114, 114'. This creates two tabs 115, 116, which can be spread apart in such a way that the screw 13 is held by its collar during its insertion. The bushing 111 is displaceable on the shaft 113 of the screwdriving instrument. Once the screw 13 is inserted, the bushing 111 is displaced upward on the shaft 113, so that the tabs 115, 116 let go of the screw 13.

A third and fourth exemplary embodiment of an intravertebral implant according to the present invention, which are likewise functionally identical to one another, are shown in FIGS. 22–26 and 27–31, respectively. Identical parts are identified by the same reference numerals. It is approximately 25 mm long and has a diameter of approximately 10–14 mm. This exemplary embodiment again has a hollow chamber 52, a dome 52, four side faces 54, 55, 56, 57, and one back face 58. Oval openings 59, 59', 60, 60' are let into all the side faces 54, 55, 56, 57. The dome 53 has a bore 63 with a female thread 64. An indentation 83 and a through opening 61 are provided in the back face 58 as well. Thus as can be seen from FIG. 8, bearing faces 67 and 68 that merge with one another are created, and in the compressed state of the hollow body 5 (FIG. 8), the bearing face 68 (formed by the indentation 83) has a larger diameter and tapers conically, while the bearing face 67 (formed by the bore 61) has a smaller diameter and forms the actual through opening 61.

The two opposed side faces 56, 57 are divided each by a respective slot 65, 66. Each slot extends from the edge where the back face 58 merges with the corresponding side face 56, 57 to the openings 60, 60' in the side faces 56, 57. On the thus-created halves of the back face 58, the bearing faces 67, 68 are thereby divided in half as well.

In the vicinity of the end facing the dome 53, two cramps 69, 70, 71, 72 are formed integrally onto each of the side faces 54, 55 that extend parallel to the slots 65, 66 and are not divided in half. These cramps are again triangular in cross section, and their free edges 73, 74, 75, 76 protrude outward by approximately 2 mm from the side faces 54, 55. These edges are embodied as sharp also, for instance being ground down, and form the aforementioned fixation elements.

In FIGS. 25 and 30, a screw 77 with a shaft 78 and a male thread 79 is shown, whose end 82 is screwed into the female thread 64 of the bore 63. The head 80 has a hexagonal socket 81 and rests with its outer circumferential face on the bearing face 68.

The difference between these exemplary embodiments is again that the third exemplary embodiment (FIGS. 22–26) has four flat side faces 54–57, while the fourth exemplary embodiment again has a completely curved, convex contour and has a "crowned" or "bellied" appearance.

The mode of operation of the third and fourth exemplary embodiment is as follows: The situation at the outset can be seen from FIGS. 22 and 23, and FIGS. 27 and 28, respectively. The side faces 54, 55 are pressed together, so that the edges of the slots 65, 66 rest on one another in narrowed fashion toward the back face 68 (or are spaced apart only slightly), and the cramps 69, 70, 71, 72 are retracted somewhat with regard to an imaginary line extending the parallel portions of the side faces 56, 57. This is the insertion position. As already noted above, in this position the inner bearing face 67 forms a circular-cylindrical passage (see FIGS. 23 and 28).

Figure 32:
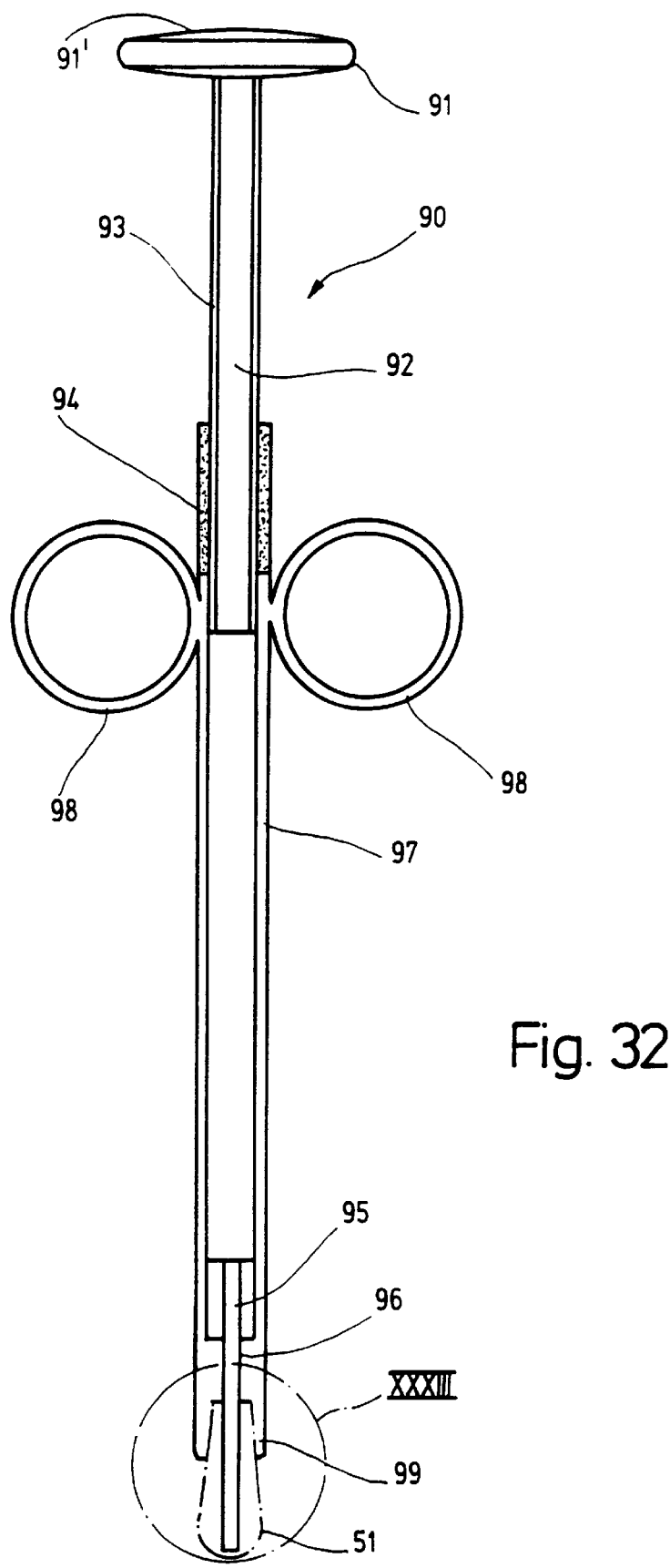
FIG. 32, which is an insertion instrument (impactor) for the exemplary embodiments of FIGS. 22–31.

For the implantation, the impacter 90 of FIG. 32 is used. It has a handle 91 and a shaft 92 provided with a male thread 93. An adjusting nut 94 is seated on the shaft 92. The shaft 92 is penetrated by a threaded spindle 95, which is provided with a male thread 96 on its end. The threaded spindle may be turned with the grip 91. It acts as an implant holder; that is, it is screwed into the bore 63 on the dome 53 of the hollow body 51. A mount 97 is displaceably held on the shaft 92; on its upper end it has two grips 98, and a bushing 99 is formed onto its lower end and encompassingly engages the hollow body 51 in the state in which it is inserted between vertebral bodies.

Figure 33:
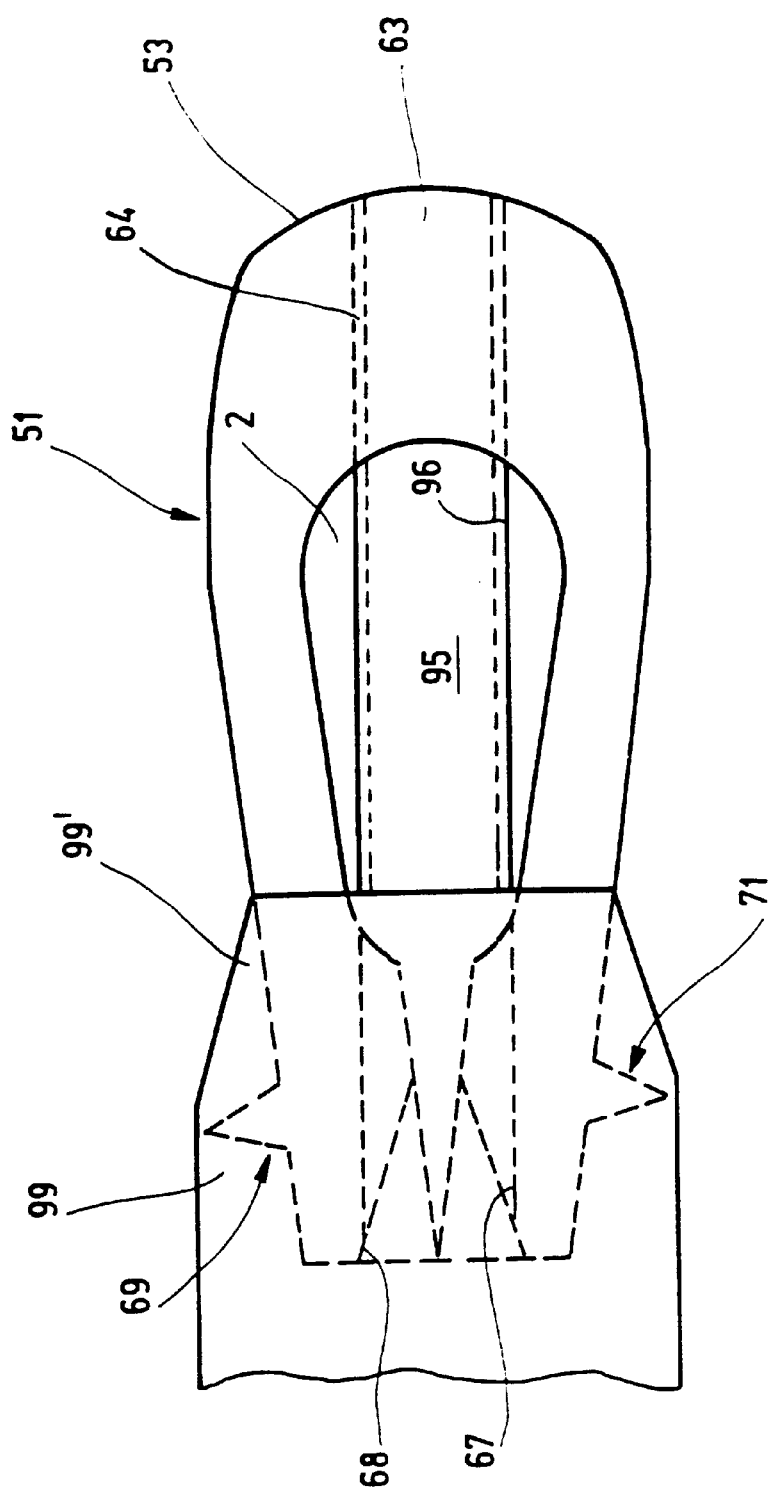
FIGS. 33—34, which shows details of the mounting in the exemplary embodiment of FIGS. 27–31, corresponding to the detail XXXIII of FIG. 32 (FIG. 34 is rotated 90° compared to FIG. 33)
Figure 34:
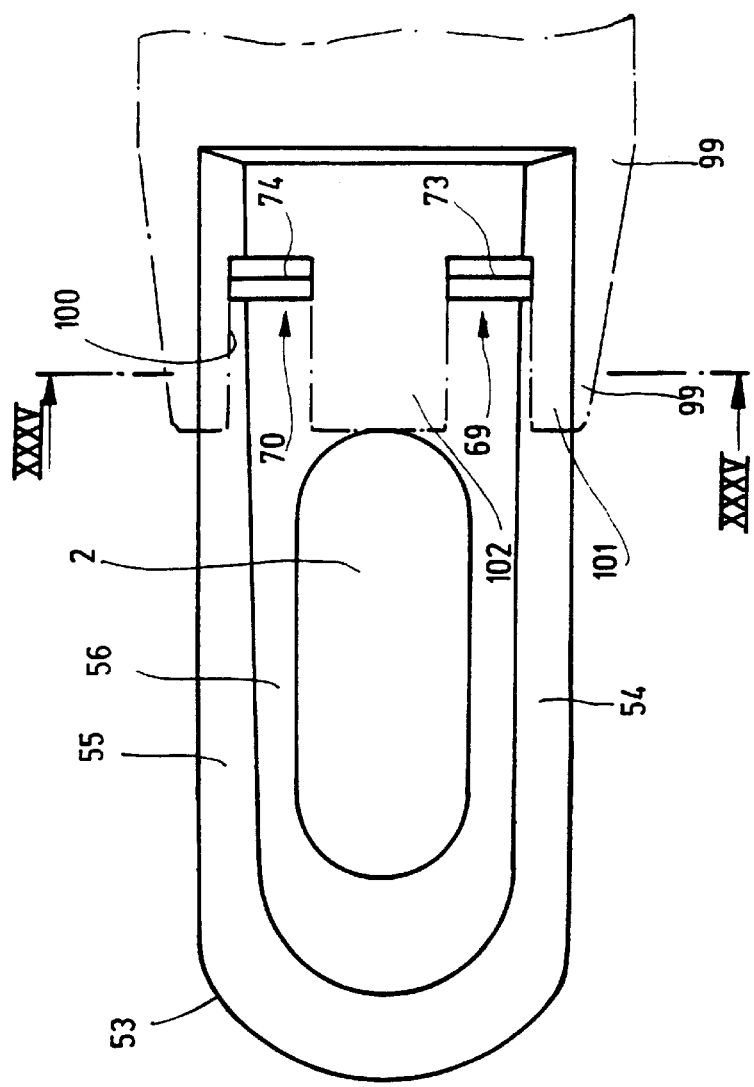
Figure 35:
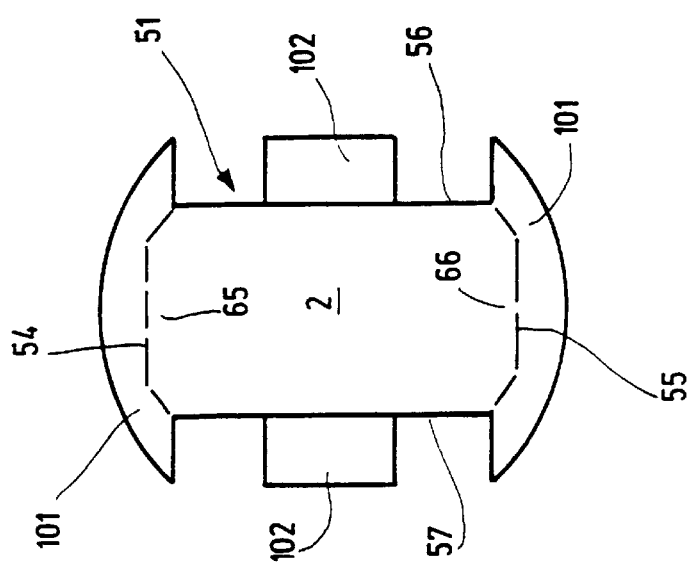
FIG. 35, which is a view in the direction of the arrows XXXV—XXXV of FIG. 34.

The way in which this encompassing engagement is accomplished is illustrated in FIGS. 33–35, which show the fourth exemplary embodiment. From FIG. 33 it can be seen that the bushing 99 completely encloses the cramps 69, 70, 71, 72 and is flattened toward its end 99', thus assuring a smooth transition between the bushing 99 and the hollow body 51. The threaded spindle 95 penetrates the hollow chamber 2 and is screwed by its end into the bore 63 on the dome 53 of the hollow body 51. FIG. 34 shows this state in a view rotated by 90°; it can be seen that the end 99' has recesses 100 which receive the cramps 69, 70, 71, 72. As a result, the end 99' of the bushing 99 is divided up into two side regions 101 and two narrow regions 102, which encompass the hollow body 51 and hold it firmly in the insertion position.

The intravertebral implant (hollow body 51) now thus fixed in its insertion position is then driven in between two vertebral bodies, for instance being hammered in, for which purpose the impact face 91' of the grip 91 is needed. Once the intravertebral implant is positioned, the adjusting nut 94 is loosened, and the mount 97 is grasped by the grips 98 and pulled upward. The threaded spindle 95 is then unscrewed out of the bore 63. Next, the intravertebral implant (hollow body 1) is widened.

This is done in such a way that the screw 77 shown in FIG. 9 is placed with its hexagonal socket 81 on the end of the screwdriver instrument 42 (see FIG. 12). The screw forms the expansion element. By fine-tuning of the dimensions, care must be taken that the screw 77 is held is in this position by gentle clamping. Then, with the aid of the screwdriver instrument 42, the screw 77 is guided in the hollow body 51, and then the end 82 in the screw 77 is then screwed into the female thread 64 of the bore 63, until the outer circumferential face of the head 40, by contact with the bearing face 68, has forced the side faces 54 and 57 apart (or more or less widely apart) into the position shown in FIG. 9, in which the cramps 69–72 have dug into the vertebral bodies. The screwdriver instrument 42 is then removed. In this way, variable expansions of the hollow body 51, which is the intravertebral implant, can thus be achieved.

Figure 36:
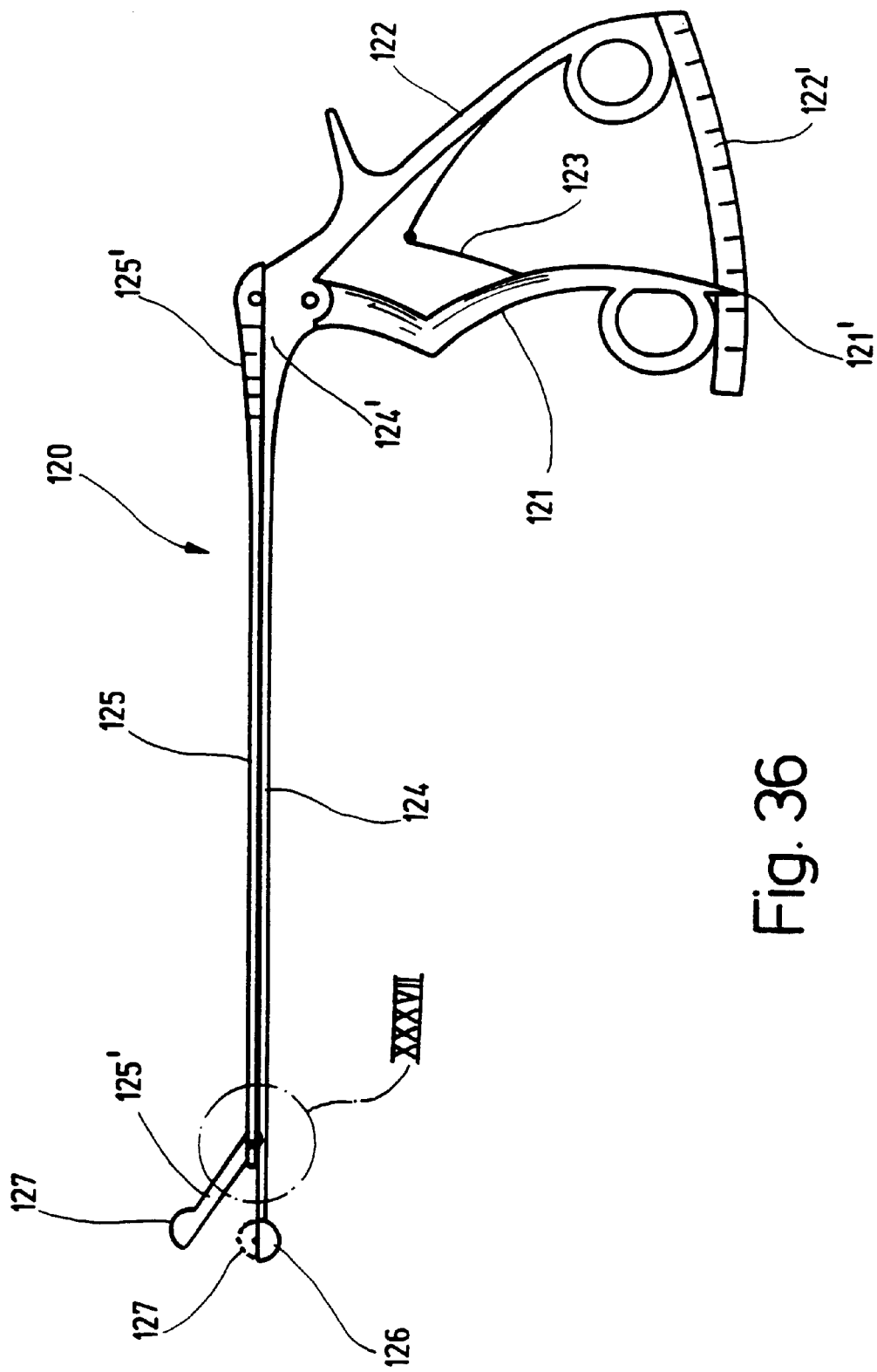
FIG. 36, which is a schematic view of an instrument for measuring the spacing between two vertebral bodies.

FIG. 36 shows a measuring instrument 120 for measuring the spacing between two vertebral bodies. Before an intravertebral implant is implanted, the spacing between two vertebral bodies must be measured, in order to be able to determine the size of implant required (see the view in FIG. 9). The adjustability of the intravertebral implant according to the invention affords a play of a few millimeters. In patients of different body sizes (for instance, women and men), this play is not enough. In these cases, a preselection among various sizes of intravertebral implant must be made.

Figure 37:
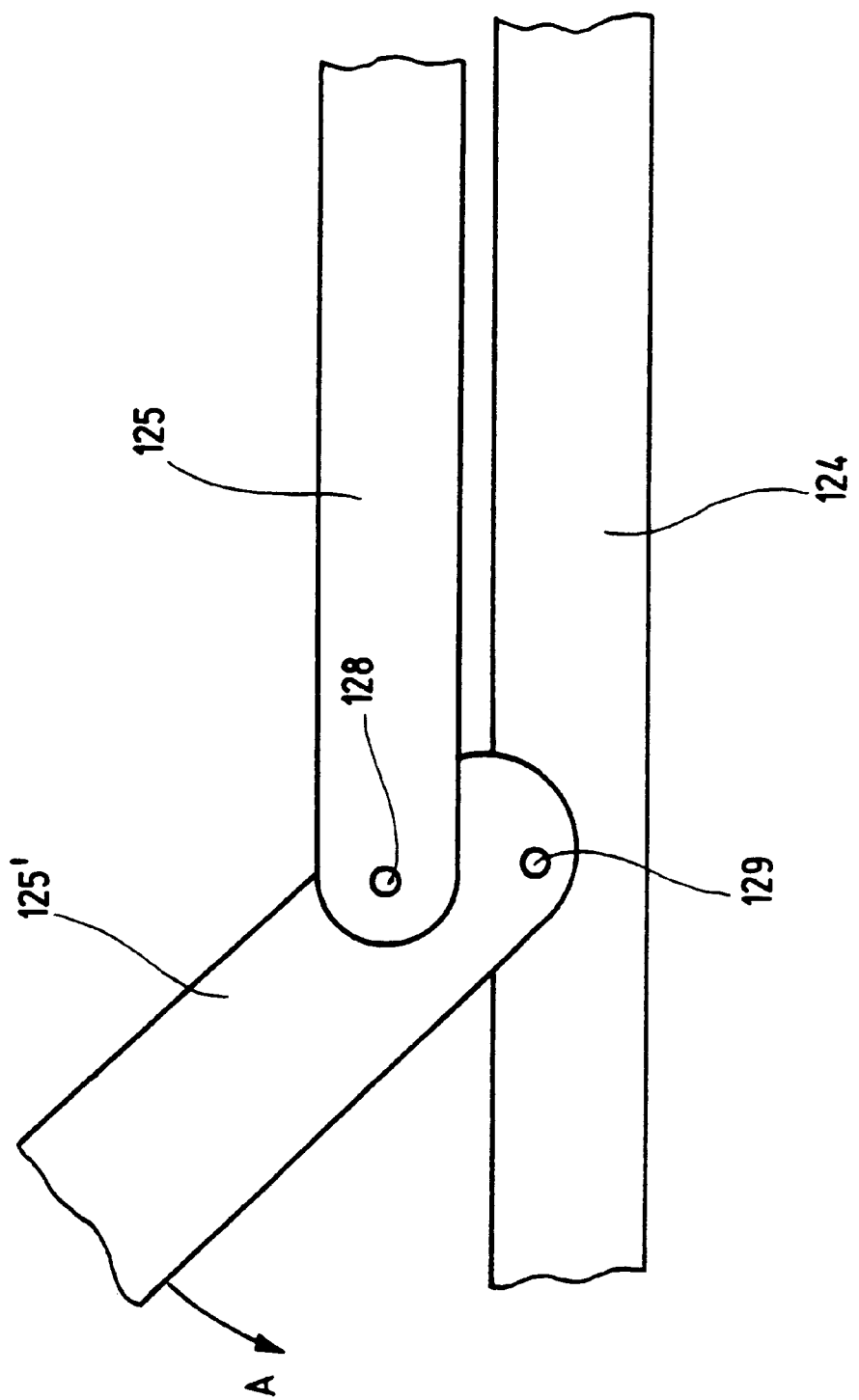
FIG. 37, which is an enlargement of detail XXXVII of FIG. 36.

The measuring instrument 120 has two grips 121, 122, which are held apart from one another by a spring 123. The two grips 121, 122 are each joined to a respective shaft 124, 125. The shaft 125 is pivotably connected to a further, shorter shaft 125'. Together, the shafts 125, 125' have the same length as the single shaft 124. The shafts 124 and 125' end in two hemispherical parts 126, 127. These parts 126, 127 act as measurement probes. In the relaxed state shown in FIG. 36, the hemispherical parts 126, 127 have already been expanded. Moving the grips 121, 122 toward one another causes the hemispheres 126, 127 to approach one another, as indicated by dashed lines in FIG. 36. The mechanical connection that effects this movement together is shown in greater clarity again in FIG. 37. By pressing the grips 121, 122 together, the shaft 125 is moved forward, that is, in the direction of the hemisphere 126. In the process it takes the shaft 125', which ends in the hemisphere 127, along with it. In this process the shaft 1251 rotates in the joint 128. However, since the shaft 125' is also pivotably connected to the shaft 124 at the joint 129, it does not move forward with the shaft 125 but instead is moved downward in the direction of the arrow A.

With the hemispherical parts 126, 127, one enters the interstice between two vertebral bodies, and then expands them again by relaxing the grips 121, 122. The measured spacing can be read out in various ways. Two of these ways are suggested in FIG. 36. A strip 122' with a scale can be attached to the grip 122, while the grip 121 is equipped with a pointer 121'. The greater the measured spacing, the greater becomes the spacing between the grip 121 and the grip 122. This spacing can be read off from the scale. Another option is a scale 125' on the end of the shaft 125. In this case, the extent of forward motion of the shaft 125 compared to the shaft 124 is a standard for the measured spacing between the vertebral bodies. The distance traveled can be read off from the scale 125', via a point 124' permanently marked onto the shaft 124.

What is claimed is:

1. An intravertebral implant, comprising:
a body having an opening provided with an interior thread;
an expansion element in the form of a screw which is screwed into said opening in engagement with said interior thread, said screw having a leading end,
wherein said body has two opposed expandable areas provided with fixation elements to fix the implant to vertebral bodies, said expandable areas each having a connected end and a free end, such that said expandable areas are connected to each other at their connected ends while their free ends are expandable by said leading end of said expansion element.

2. The intravertebral implant as defined in claim 1, wherein said body comprises an essentially cylindrical, hollow shape with opposing faces, and wherein said expandable areas are provided in said opposing faces.

3. The intravertebral implant as defined in claim 2, wherein said body has a rearward face, and wherein said opening is provided in said rearward face.

4. The intravertebral implant as defined in claim 3, wherein said body has a forward end having a dome-like member, and wherein said expandable members are connected with each other through said dome-like member.

5. The intravertebral implant as defined in claim 4, wherein said expandable areas comprise tongues located in said opposing faces.

6. The intravertebral implant as defined in claim 5, wherein said tongues are formed in said respective faces by U-shaped slots.

7. The intravertebral implant as defined in claim 3, wherein each expandable area is provided with a step which are acted upon to return to their original position by a retrieval instrument inserted in said opening.

8. The intravertebral implant as defined in claim 7, wherein said steps are provided at said free ends of said expandable areas.

9. The intravertebral implant as defined in claim 7, wherein said steps each have means to prevent an inserted retrieval instrument from slipping off of said step.

10. The intravertebral implant as defined in claim 3, wherein said screw is provided with a conically tapered end.

11. The intravertebral implant as defined in claim 1, wherein the implant has a convex contour.

12. The intravertebral implant as defined in claim 1, wherein said body has a dome-like member to which said expandable areas are connected at their connected ends, and from which slots extend which separate said expandable areas, wherein said opening for receiving said screw is provided in said dome-like member, and wherein said free ends of said expandable areas form a throughway in their non-expandable position through which said screw extends, when screwed into said opening.

13. The intravertebral implant as defined in claim 12, wherein said screw is conically tapered in the longitudinal direction of said body.

14. The intravertebral implant as defined in claim 12, wherein the surface of said body which cooperates with said screw is conically tapered in the longitudinal direction of said body.

15. The intravertebral implant as defined in claim 1, wherein said opening is suited for receiving an implant holder.

* * * * *